(12) United States Patent
Fichot et al.

(10) Patent No.: US 9,462,821 B2
(45) Date of Patent: Oct. 11, 2016

(54) MODULATION OF INFANT FAT MASS

(75) Inventors: Marie-Claire Fichot, Blonay (CH); Catherine Mace, Lausanne (CH); Philippe Steenhout, La Tour-de-Peilz (CH)

(73) Assignee: Nestec S.A., Vevey (CH)

( * ) Notice: Subject to any disclaimer, the term of this patent is extended or adjusted under 35 U.S.C. 154(b) by 1034 days.

(21) Appl. No.: 13/133,295

(22) PCT Filed: Nov. 23, 2009

(86) PCT No.: PCT/EP2009/065662
§ 371 (c)(1),
(2), (4) Date: Jun. 7, 2011

(87) PCT Pub. No.: WO2010/066569
PCT Pub. Date: Jun. 17, 2010

(65) Prior Publication Data
US 2011/0244072 A1   Oct. 6, 2011

(30) Foreign Application Priority Data
Dec. 8, 2008 (EP) .................................. 08170936

(51) Int. Cl.
| | |
|---|---|
| A23C 9/00 | (2006.01) |
| A23L 1/29 | (2006.01) |
| A23L 1/30 | (2006.01) |
| A23L 1/302 | (2006.01) |
| A23L 1/304 | (2006.01) |
| A23L 1/305 | (2006.01) |

(52) U.S. Cl.
CPC ............ *A23L 1/296* (2013.01); *A23L 1/302* (2013.01); *A23L 1/304* (2013.01); *A23L 1/305* (2013.01); *A23L 1/3008* (2013.01); *A23L 1/3053* (2013.01); *A23V 2002/00* (2013.01)

(58) Field of Classification Search
USPC ........................................................ 426/656
See application file for complete search history.

(56) References Cited

U.S. PATENT DOCUMENTS

| | | | | |
|---|---|---|---|---|
| 6,162,472 A | * | 12/2000 | Griffin et al. | 426/42 |
| 2003/0050341 A1 | * | 3/2003 | Bydlon et al. | 514/560 |
| 2007/0026049 A1 | * | 2/2007 | Auestad et al. | 424/439 |

FOREIGN PATENT DOCUMENTS

| | | |
|---|---|---|
| EP | 1 932 437 | 6/2008 |
| WO | 2006069918 | 7/2006 |
| WO | 2007004878 | 1/2007 |
| WO | 2007073192 | 6/2007 |
| WO | 2007135141 | 11/2007 |

OTHER PUBLICATIONS

International Search Report for PCT/EP2009/065662 mailing date May 10, 2010—10 pages.

* cited by examiner

*Primary Examiner* — Elizabeth Gwartney
(74) *Attorney, Agent, or Firm* — K&L Gates LLP

(57) ABSTRACT

A method of reducing the accumulation of fat mass in a neonatal human infant at risk thereof which method comprises administering to the infant during at least a part of the neonatal period a therapeutic amount of a nutritional composition comprising proteins in an amount such that the composition contains more than 2.4 g of protein per 100 kcal. As weight gain during the first week of life has been associated with overweight in adulthood, this may offer a method of reducing the risk of developing obesity in later life. Also claimed is the administration of DHA to the mother during gestation period.

19 Claims, 4 Drawing Sheets

Fat mass of 2 weeks-old infants breastfed (Reference) or fed a formula with 1.83g protein/100 kcal (F1.8 group) or 2.7g protein/100kcal (F2.7 group).

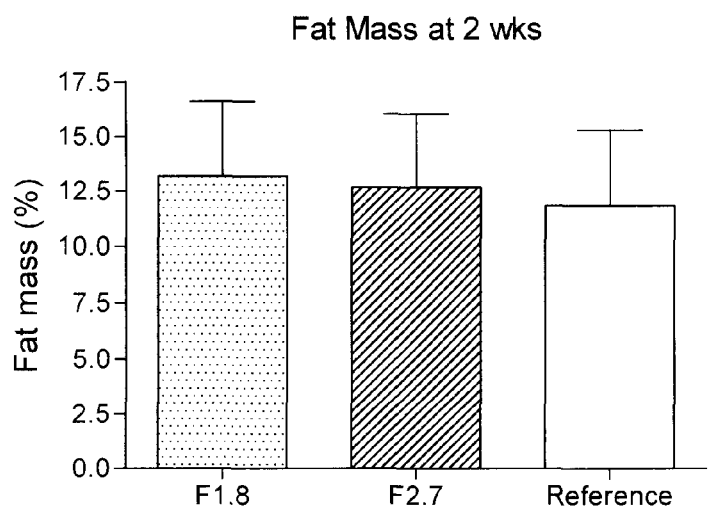
Figure 1: Fat mass of 2 weeks-old infants breastfed (Reference) or fed a formula with 1.83g protein/100 kcal (F1.8 group) or 2.7g protein/100kcal (F2.7 group).

Figure 2: Body weight of 2 days-old pups
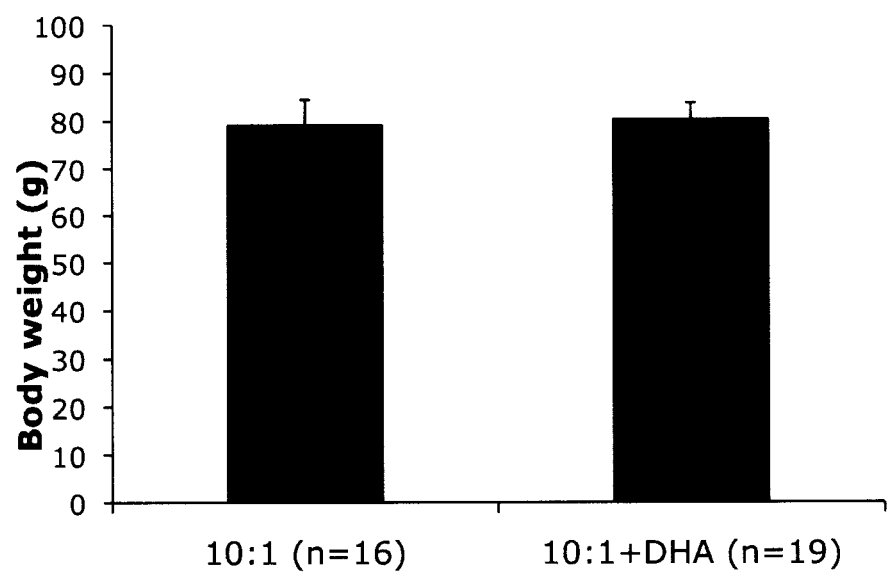

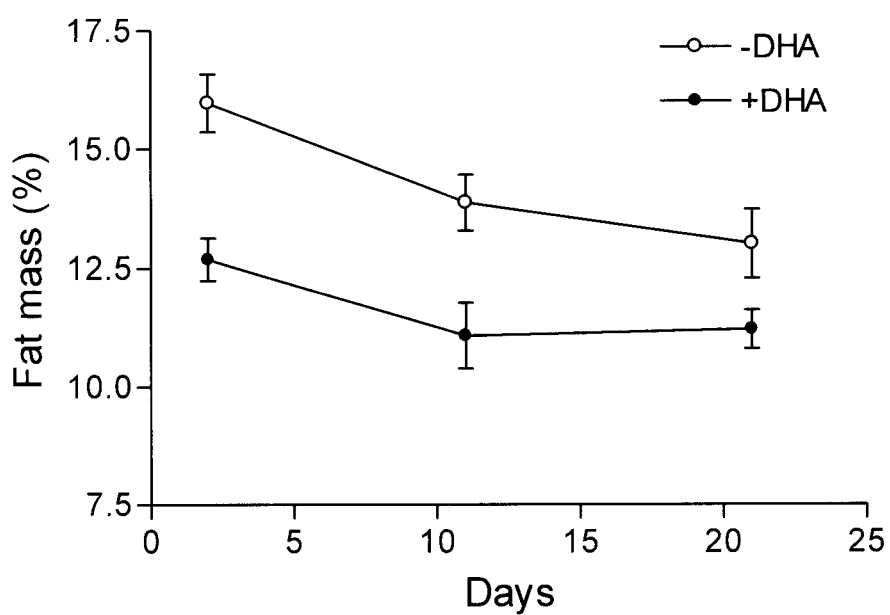
Figure 3: Body fat mass of 2-, 11- and 21 days-old pups

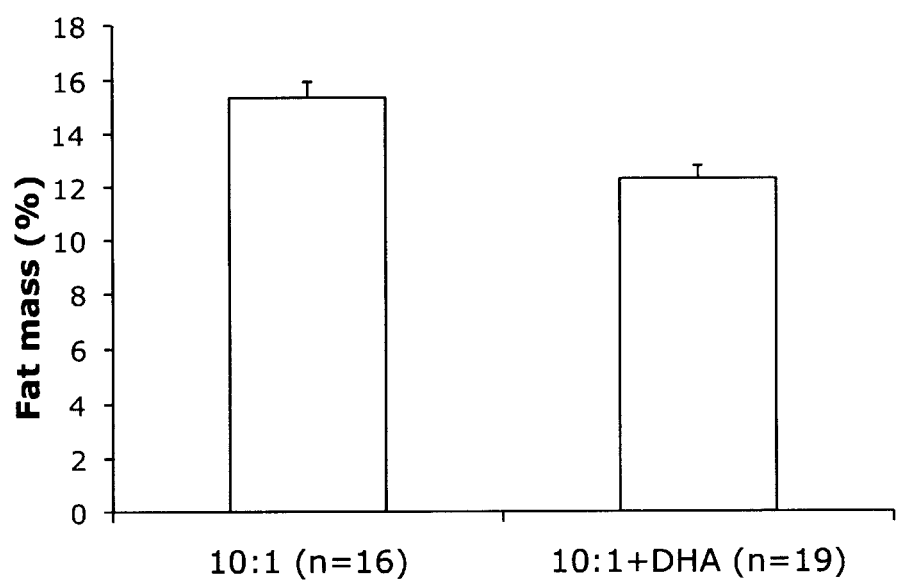
Figure 4: Body fat mass of 2 days-old pups

MODULATION OF INFANT FAT MASS

This invention relates to the modulation of infant fat mass.

Mother's milk is recommended for all infants. However, in some cases breast feeding is inadequate or unsuccessful or inadvisable for medical reasons or the mother chooses not to breast feed. Infant formulas have been developed for these situations. Greater knowledge of the composition of human milk affords the opportunity to design infant formulas that are closer in composition to human milk. Particular consideration has been given to devising formulas consumption of which results in growth and metabolic patterns similar to those of breastfed infants, in the hope that this will result in the development of similar health characteristics in later childhood and adulthood.

Conventional infant formulas fall into two categories, starter formulas for infants from the age of birth to 4 to 6 months and which provide complete nutrition for this age group and so-called follow-on formulas for infants between the ages of four to six months and twelve months which are fed to the infants in combination with increasing amounts of other foods such as infant cereals and puréed fruits, vegetables and other foodstuffs as the process of weaning progresses.

Dietary protein provides the essential amino acids necessary for protein synthesis and growth and, in infant formula, both protein quality and protein quantity are important. Infant formulas are usually based on cows' milk but the amino acid profile of cows' milk is noticeably different from that of human milk. In the past, in order to supply enough of the essential amino acids, infant formulas based on cows' milk had to have a protein content significantly higher than that of the human milk, which, in fact, has the lowest protein concentration found in any mammal ranging from 1.4 to 1.8 g per 100 kcal for mature human milk. Over the past 5 to 10 years, this has led to a tendency to decrease the protein content in infant formulas. For example, in EP 1220620, an infant formula composition is proposed in which the protein amounts to between 9.0 and 10.0% on a weight for weight basis. This corresponds to about 1.8 g protein/100 kcal which is comparable to the level of protein in mature human milk.

Typically, the protein content of infant formulas is between 1.8 and 3.5 g/100 kcal with the protein content of starter formulas being towards the lower end of the range and the protein content of follow-on formulas being toward the upper end of the range. For example, the protein content of Nestlé NAN 1® starter infant formula is 1.83 g/100 kcal and the protein content of Nestlé NAN 2® follow-on infant formula is 3.1 g/100 kcal.

Certain benefits have been shown to be associated with feeding starter infant formulas with about 1.8 g protein/100 kcal to infants during the first few months of life. For example, according to WO2006/069918, the evolution of plasma IGF-1 levels in infants fed with an infant formula containing 1.83 g protein/100 kcal was closer to that of breast fed infants over the first few months of life than was that of infants fed an infant formula containing 2.39 g protein/100 kcal.

It has been demonstrated in infant monkeys that reducing the protein content of the formula results in a growth pattern and early age insulin and glucose metabolism more similar to that of a control breast fed group than to those of groups fed formula with higher protein contents. The implication is that increased IGF-1 levels may result in a different body composition and an increased predisposition to obesity in later life. Childhood overweight and obesity currently affects 18 million children under age 5 worldwide. Almost 30% of US children and adolescents and between 10 and 30% of European children are overweight or obese.

There is, therefore, clearly a need for further investigation into the impact of early nutrition on body composition in infancy and on the risk of developing obesity later in life.

SUMMARY OF THE INVENTION

It has now surprisingly been found that feeding an infant formula with a relatively high protein content during the neonatal period may reduce fat mass accumulated during the neonatal period (compared to fat mass accumulated by infants fed an infant formula with a lower protein content during the same period).

Accordingly, the present invention provides the use of a source of proteins for the preparation of nutritional composition for administration to a human infant during at least a part of the neonatal period so as to reduce the accumulation of fat mass in the neonatal period wherein the composition contains at least 2.4 g of protein per 100 kcal.

The invention also extends to the use of a source of proteins for the preparation of nutritional composition for administration to a human infant during at least a part of the neonatal period so as to reduce the risk of development of obesity later in life wherein the composition contains at least 2.4 g of protein per 100 kcal.

The invention further extends to a method of reducing the accumulation of fat mass in a neonatal human infant at risk thereof which method comprises administering to the infant during at least a part of the neonatal period a therapeutic amount of a nutritional composition comprising proteins in an amount such that the composition contains more than 2.4 g of protein per 100 kcal.

The invention also extends to a method of reducing the possibility that an infant will develop obesity later in life comprising feeding to the infant during at least a part of the neonatal period a nutritional composition comprising proteins in an amount such that the composition contains more than 2.4 g of protein per 100 kcal.

Weight gain during the first week of life has been associated with overweight in adulthood (Stettler N, Stallings V A, Troxel A B, Zhao J, Schinnar R, Nelson S E, Ziegler E E, Strom B L. Weight gain in the first week of life and overweight in adulthood: a cohort study of European American subjects fed infant formula. Circulation (2005). 111: 1897-903). It therefore follows that a nutritional intervention which reduces accumulation of fat mass in the neonatal period—or, in other words, results in an accumulation of fat mass during the neonatal period which mimics that of a breast fed infant—may reduce the risk of overweight and obesity later in life.

DETAILED DESCRIPTION OF THE INVENTION

In this specification, the following expressions have the following meanings:—

"Infant" means a child under the age of 12 months;

"Neonatal infant" means an infant in the first month of life;

"Neonatal period" means the first month of life.

All percentages and ratios are by weight unless otherwise specified.

References to the energy density of the nutritional composition in a specified number of kilocalories per liter refer, in the context of powdered products, to the product after re-constitution according to the directions provided with the product.

Preferably the nutritional composition for use in the present invention contains between 2.4 and 3.0 g protein/100 kcal, more preferably between 2.4 and 2.8 g/100 kcal.

Preferably the nutritional composition containing more than 2.4 g of protein/100 kcal is fed to the infant for at least the first two weeks of life. Optionally feeding with the said composition may continue for the whole of the neonatal period whereafter the infant may be fed with a nutritional composition containing from 1.7 to 2.0 g protein/100 kcal.

The source of the protein is not believed to be critical to the present invention provided that the minimum requirements for essential amino acid content are met and satisfactory growth is ensured. Thus, protein sources based on cows' milk proteins such as whey, casein and mixtures thereof may be used as well as protein sources based on soy. As far as whey proteins are concerned, the protein source may be based on acid whey or sweet whey, whey protein isolate or mixtures thereof and may include alpha-lactalbumin and beta-lactoglobulin in whatever proportions are desired.

Preferably, however, the protein source is based on modified sweet whey. Sweet whey is a readily available by-product of cheese making and is frequently used in the manufacture of infant formulas based on cows' milk. However, sweet whey includes a component which is undesirably rich in threonine and poor in tryptophan called caseino-glyco-macropeptide (CGMP). Removal of the CGMP from sweet whey results in a protein with a threonine content closer to that of human milk. This modified sweet whey can then be supplemented with those amino acids in respect of which it has a low content (principally histidine, arginine and tryptophan). A process for removing CGMP from sweet whey is described in EP 880902 and an infant formula based on this modified sweet whey is described in WO 01/11990. Such protein sources have been shown in animal and human studies to have a protein efficiency ratio, nitrogen digestibility, biological value and net protein utilisation comparable to standard whey-adapted protein sources with a much higher protein content per 100 kcal and to result in satisfactory growth. If modified sweet whey is used as the protein source, it is may be supplemented by free arginine in an amount of from 0.1 to 3% by weight and/or free histidine in an amount of from 0.1 to 1.5% by weight.

The proteins may be intact or hydrolysed or a mixture of intact and hydrolysed proteins although intact proteins are generally preferred. However, it may be desirable to supply partially hydrolysed proteins (degree of hydrolysis between 2 and 20%), for example for infants believed to be at risk of developing cows' milk allergy. If hydrolysed proteins are required, the protein source may be hydrolysed as desired and as is known in the art. For example, a whey protein hydrolysate may be prepared by enzymatically hydrolysing the whey fraction in two steps as disclosed in EP 322589. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

Preferably the nutritional composition for use in the present invention is an infant formula. Such a nutritionally complete composition will also contain other ingredients of the type conventionally found in infant formulas such as carbohydrates, fats, vitamins and minerals as well as semi-essential nutrients.

The preferred source of carbohydrates is lactose although other carbohydrates such as saccharose, maltodextrin, and starch may also be added. Preferably carbohydrate sources contribute between 35 and 65% of the total energy of the formula The lipid source may be any lipid or fat which is suitable for use in infant formulas. Preferred fat sources include palm olein, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example about 8:1 to about 10:1.

The infant formula will also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin $B_1$, vitamin $B_2$, vitamin $B_6$, vitamin $B_{12}$, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the infant formula may contain emulsifiers and stabilisers such as soy lecithin, citric acid esters of mono- and di-glycerides, and the like. This is especially the case if the formula is provided in liquid form.

The infant formula may optionally contain other substances which may have a beneficial effect such as fibres, lactoferrin, nucleotides, nucleosides, and the like. Probiotic bacteria such as *Lactobacillus rhamnosus* ATCC 53103, *Lactobacillus rhamnosus* CGMCC 1.3724, *Lactobacillus reuteri* ATCC 55730, *Lactobacillus reuteri* DSM 17938, *Bifidobacterium lactis* CNCM I-3446, *Bifidobacterium longum* ATCC BAA-999, the strain of *Bifidobacterium breve* sold by Danisco under the trade mark Bb-03, the strain of *Bifidobacterium breve* sold by Morinaga under the trade mark M-16V, the strain of *Bifidobacterium breve* sold by Institut Rosell (Lallemand) under the trade mark R0070 and the strain of *Bifidobacterium infantis* sold by Procter & Gamble Co. under the trade mark Bifantis may also be included The infant formula may be prepared in any suitable manner. For example, an infant formula may be prepared by blending together the protein source, the carbohydrate source, and the fat source in appropriate proportions. If used, emulsifiers may be included in the blend at this stage. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes.

This may be carried out by steam injection or by heat exchanger; for example a plate heat exchanger.

The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled and any heat sensitive components; such as vitamins and minerals may be added. The pH and solids content of the homogenised mixture is conveniently standardised at this point.

If it is desired to produce a powdered infant formula, the homogenised mixture is transferred to a suitable drying apparatus such as a spray drier or freeze drier and converted to powder. The powder should have a moisture content of less than about 5% by weight.

If it is desired to produce a liquid infant formula, the homogenised mixture is filled into suitable containers; preferably aseptically. However, the liquid infant formula may also be retorted in the container. Suitable apparatus for carrying out filling of this nature is commercially available. The liquid infant formula may be in the form of a ready to feed formula having a solids content of about 10 to about 14% by weight or may be in the form of a concentrate; usually of solids content of about 20 to about 26% by weight.

In one embodiment of the invention, DHA (docosahexaenoic acid) is used as part of the composition of the invention, especially during perinatal period. This may include both the supplementation of the pregnant mothers with DHA and/or the administration of DHA to the young infants during the perinatal period (preferably between birth and 6 months of age, between birth and 3 months of age, between birth and 4 weeks of age, or between birth and 1 week of age). It has been evidenced (see example 3) that such administration of DHA has a positive effect on the fat mass of the infants after birth. In one embodiment the invention comprises both the use and administration of the above described proteinic features and the administration of DHA. In one embodiment the DHA (docosahexaenoic acid) is administered to the infant. In one embodiment the DHA (docosahexaenoic acid) is administered to the mother during the gestation period, preferably during the last 6 months, last 3 months, last 4 weeks, or last week of the gestation period. In one embodiment the DHA is administered to both the mother during the gestation period (preferably according to the regimen above) and to the infant after birth (preferably according to the regimen above).

In one embodiment the DHA is comprised in the diet at a level of between 0.1% and 4%, preferably between 0.3% and 2.5%, most preferably between 0.5 and 1%, In one embodiment the supplementation is at 0.75% DHASCO oil (corresponding to 2.4% DHA of total fatty acids).

In one embodiment the invention comprises a composition according as described above for administration to infants during perinatal period, for obtaining a low fat body mass accumulation during the neonatal period.

In one embodiment the invention comprises a kit of part comprising a composition to be administered to the infant as described above and also comprising a composition for administration to pregnant female, preferably during the last 6 months, last 3 months or last 4 weeks of the gestational period, for helping obtaining a low fat body mass accumulation in the infant during the neonatal period.

In one embodiment the low body mass accumulation is cited in comparison to the average fat body mass accumulation obtained in infants receiving a regular diet.

The invention will now be further illustrated by reference to the following examples.

Example 1

An example of the composition of a suitable infant formula to be used in the present invention is given below:—

| Nutrient | per 100 kcal | per litre |
|---|---|---|
| Energy (kcal) | 100 | 670 |
| Protein (g) | 2.70 | 18.1 |
| Fat (g) | 5.3 | 35.5 |
| Linoleic acid (g) | 0.76 | 5.1 |
| α-Linolenic acid (mg) | 95 | 635 |
| Lactose (g) | 10.38 | 69.6 |
| Minerals (g) | 0.45 | 3.0 |
| Na (mg) | 26 | 180 |
| K (mg) | 89 | 600 |
| Cl (mg) | 64 | 430 |
| Ca (mg) | 80 | 540 |
| P (mg) | 40 | 270 |
| Mg (mg) | 7 | 47 |
| Mn (μg) | 8 | 50 |
| Se (μg) | 2 | 14 |
| Vitamin A (μg RE) | 105 | 540 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |

The following example is given by way of illustration only and should not be construed as limiting the subject-matter of the present application.

Example 2

Effect of the Level of Dietary Protein in the Neonatal Period on Infant Body Composition This example demonstrates the effect of the protein content of an infant formula used as the sole source of nutrition for a group of infants for the first month of their life on their body composition.

A randomized, controlled, double-blinded study of three groups in parallel (being two experimental groups each of which was fed a different infant formula as described in more detail below and a third group of wholly breast-fed infants as a reference) and was carried out at the Réanimation Néonatale et Néonatologie, Hôpital de la Croix Rousse, Lyon, France in accordance with the principles established in the 1964 Declaration of Helsinki (as amended) and with the approval of the CCPPRB Lyon A.

Only healthy newborn infants with healthy mothers having a normal BMI before pregnancy and not having diabetes were considered for inclusion. Infants meeting these criteria whose mothers had decided not to breast feed at all for the first four months of the life of their infant were randomly assigned to one of the two experimental groups. Infants whose mothers had decided to breast feed exclusively for the first three months of the life of their infant were assigned to the reference group.

Of the experimental groups, one was fed the formula with 2.7 g protein/100 kcal (F2.7 group) and the other was fed a formula with 1.83 g protein/100 kcal (F1.8 group). Detailed compositions of the formulas are given in the table below.

| Nutrient | F2.7 per 100 kcal | F1.8 per 100 kcal |
|---|---|---|
| Energy (kcal) | 100 | 100 |
| Protein (g) | 2.70 | 1.83 |
| Fat (g) | 5.3 | 5.34 |
| Linoleic acid (g) | 0.76 | 0.77 |
| α-Linolenic acid (mg) | 95 | 95 |
| Lactose (g) | 10.38 | 11.16 |
| Minerals (g) | 0.45 | 0.37 |
| Na (mg) | 26 | 23 |
| K (mg) | 89 | 89 |
| Cl (mg) | 64 | 64 |
| Ca (mg) | 80 | 80 |
| P (mg) | 40 | 40 |
| Mg (mg) | 7 | 6.9 |
| Mn (μg) | 8 | 8 |
| Se (μg) | 2 | 2 |
| Vitamin A (μg RE) | 105 | 105 |
| Vitamin D (μg) | 1.5 | 1.5 |
| Vitamin E (mg TE) | 0.8 | 0.8 |
| Vitamin K1 (μg) | 8 | 8 |
| Vitamin C (mg) | 10 | 10 |
| Vitamin B1 (mg) | 0.07 | 0.07 |
| Vitamin B2 (mg) | 0.15 | 0.15 |
| Niacin (mg) | 1 | 1 |
| Vitamin B6 (mg) | 0.075 | 0.075 |
| Folic acid (μg) | 9 | 9 |
| Pantothenic acid (mg) | 0.45 | 0.45 |
| Vitamin B12 (μg) | 0.3 | 0.3 |
| Biotin (μg) | 2.2 | 2.2 |
| Choline (mg) | 10 | 10 |
| Fe (mg) | 1.2 | 1.2 |
| I (μg) | 15 | 15 |
| Cu (mg) | 0.06 | 0.06 |
| Zn (mg) | 0.75 | 0.75 |

The two formulas were isocaloric having an energy density of 670 kcal/liter. In both cases, the whey:casein ration was 70:30. The formulas were supplied packed in metal cans with their identity marked by a letter coding known only to the investigating staff. The duration of the study was 12 months.

238 infants (125 boys and 113 girls) were recruited, 74 to the F1.8 group, 80 to the F2.7 group and 84 to the reference group. The infants were fed their assigned formula or breast milk ad libitum as the sole source of nutrition.

Growth parameters and body composition were determined at the age of 2 weeks±2 days. Body composition (BC) measurements were used to assess fat mass (FM) gain during the first year of age using PEA-POD methodology. PEA-POD is designed to measure the BC of babies from birth to 6 months using principles similar to hydrostatic weighing (underwater weighing). Instead of using water to measure body volume, PEA-POD uses air displacement plethysmography as a densitometric technique in which body fat is assessed from direct measurement of subject mass volume to measure body volume.

The calorie intake did not differ between the formula groups and growth parameters including gain of body weight, head circumference and length were identical between the 3 groups. As shown in FIG. 1, at 2 weeks of age, the accumulated fat mass was not different between the formula-fed groups but was significantly higher in the F1.8 group compared to the reference group (fat mass: 13.2±3.4 vs 11.8±3.5%, $p<0.01$;). The F2.7 group showed no significant difference of fat mass (12.7±3.4%) when compared to the reference group (see FIG. 1).

These results show that protein intake during the first 2 weeks of life does not impact growth parameters. However, a low protein intake leads to an increased adiposity when compared to breastfeeding.

Example 3

Maternal and Perinatal DHA Supplementation Reduces Fat Mass in the Neonate Guinea Pig In one embodiment of the invention, the effect of DHA (docosahexaenoic acid) was investigated. The effects of maternal docosahexaenoic acid (DHA) supplementation on body weight and fat mass development in the neonate guinea pig were studied. Female guinea pigs were fed a diet supplemented or not with 0.75% DHASCO oil (corresponding to 2.4% DHA of total fatty acids; DHA is available from Martek Biosciences, Columbia, Md., USA) during pregnancy and lactation. The fatty acid analysis of the dam's milk, collected 3 days after delivery, showed detectable levels of DHA (1.8% of total fatty acids) only in the supplemented group. At 2 days of age, the body weight of the offspring was identical in both groups (FIG. 2) while the % of fat mass was significantly lower in the DHA supplemented group (−DHA: 16.0±0.6%; +DHA: 12.7±0.4%, $p<0.001$) (FIG. 4). At day 21, this difference in % fat mass between groups was attenuated but still significant (FIG. 3). These results show that perinatal DHA intake reduces fat accretion during fetal life and/or the first postnatal days. Further studies will be needed for understanding the mechanism of action of DHA on adipose tissue development in early life and the consequences later on.

The invention claimed is:

1. A method for reducing the accumulation of fat mass in a human infant during at least a part of the neonatal period comprising administering a first nutritional composition comprising between 2.4 and 3.0 g of protein per 100 kcal, followed by administration of a second nutritional composition having a protein content between 1.7 and 2.0 g protein per 100 kcal for the remainder of the first four months of the life of the infant.

2. The method of claim 1, wherein the first nutritional composition comprises between 2.4 and 2.8 g of protein per 100 kcal.

3. The method of claim 1, wherein the first nutritional composition is administered to the infant for the whole of the neonatal period.

4. The method of claim 1, wherein the proteins in the first nutritional composition are intact.

5. The method of claim 1, wherein the proteins in the first nutritional composition are partially hydrolysed.

6. The method of claim 5 wherein the degree of hydrolysis of the proteins in the first nutritional composition is between 2 and 20%.

7. The method of claim 1, wherein the first nutritional composition is an infant formula.

8. The method of claim 1, wherein DHA (docosahexaenoic acid) is administered to the infant as part of the first nutritional composition.

9. The method of claim 1, wherein DHA (docosahexaenoic acid) is administered to a mother of the infant during the gestation period of the infant.

10. A method for reducing the risk of development of obesity later in life in an infant comprising administering to the infant during at least a part of the neonatal period a first nutritional composition comprising between 2.4 and 3.0 g of protein per 100 kcal, followed by administration of a second nutritional composition having a protein content between 1.7 and 2.0 g protein per 100 kcal for the remainder of the first four months of the life of the infant.

11. The method of claim 10, wherein the first nutritional composition comprises between 2.4 and 2.8 g of protein per 100 kcal.

12. The method of claim 10, wherein the first nutritional composition is administered to the infant for the whole of the neonatal period.

13. The method of claim 10, wherein the proteins in the first nutritional composition are intact.

14. The method of claim 10, wherein the proteins in the first nutritional composition are partially hydrolysed.

15. The method of claim 14, wherein the degree of hydrolysis of the proteins in the first nutritional composition is between 2 and 20%.

16. The method of claim 10, wherein the first nutritional composition is an infant formula.

17. The method of claim 10, wherein DHA (docosahexaenoic acid) is administered to the infant as part of the first nutritional composition.

18. The method of claim 10, wherein DHA (docosahexaenoic acid) is administered to a mother of the infant during the gestation period of the infant.

19. A method for obtaining a low fat body mass accumulation in an infant during the neonatal period comprising the steps of administering during at least a portion of the neonatal period a first nutritional composition comprising between 2.4 and 3.0 g of protein per 100 kcal, followed by administration of a second nutritional composition having a protein content between 1.7 and 2.0 g protein per 100 kcal for the remainder of the first four months of the life of the infant.

* * * * *